United States Patent
Koskas et al.

(10) Patent No.: US 9,308,079 B2
(45) Date of Patent: Apr. 12, 2016

(54) ENDOVASCULAR PROSTHESIS

(71) Applicants: Fabien Koskas, Paris (FR); Julien Molina, Paris (FR); Chika Cho, Paris (FR)

(72) Inventors: Fabien Koskas, Paris (FR); Julien Molina, Paris (FR); Chika Cho, Paris (FR)

(73) Assignees: ASSISTANCE PUBLIQUE-HOPITAUX DE PARIS, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 0 days.

(21) Appl. No.: 14/365,136

(22) PCT Filed: Dec. 10, 2012

(86) PCT No.: PCT/FR2012/000510
§ 371 (c)(1),
(2) Date: Aug. 11, 2014

(87) PCT Pub. No.: WO2013/088004
PCT Pub. Date: Jun. 20, 2013

(65) Prior Publication Data
US 2015/0005868 A1 Jan. 1, 2015

(30) Foreign Application Priority Data

Dec. 15, 2011 (FR) .................................. 11 03867

(51) Int. Cl.
*A61F 2/07* (2013.01)
*A61F 2/852* (2013.01)
(Continued)

(52) U.S. Cl.
CPC . *A61F 2/07* (2013.01); *A61F 2/852* (2013.01); *A61F 2/856* (2013.01); *A61F 2/90* (2013.01); *A61F 2002/061* (2013.01); *A61F 2002/075* (2013.01); *A61F 2002/828* (2013.01);
(Continued)

(58) Field of Classification Search
CPC ................. A61F 2/07; A61F 2/82; A61F 2/06
USPC ................................................ 623/1.13–1.36
See application file for complete search history.

(56) References Cited

U.S. PATENT DOCUMENTS

| 6,645,242 | B1 | 11/2003 | Quinn | |
| 8,672,993 | B2 * | 3/2014 | Chuter | ...................... A61F 2/07 623/1.13 |

(Continued)

FOREIGN PATENT DOCUMENTS

| WO | 2008/107885 | 9/2008 |
| WO | 2009/020653 | 2/2009 |

(Continued)

OTHER PUBLICATIONS

International Search Report dated Apr. 2, 2013, corresponding to PCT/FR2012/000510.

*Primary Examiner* — Suzette J Gherbi
(74) *Attorney, Agent, or Firm* — Young & Thompson

(57) ABSTRACT

The endovascular prosthesis includes a first expandable framework and a first jacket for the first framework, the first framework and the first jacket forming a first channel when the first framework is in the expanded state. The first framework and the first jacket each have at least one opening, which openings are arranged substantially opposite one another and through which a sleeve is received, the sleeve having a first end and a second end, the perimeter of the first end being attached to the perimeter of the opening of the first jacket, while the second end extends inside the first channel.

18 Claims, 4 Drawing Sheets

Figure 1:
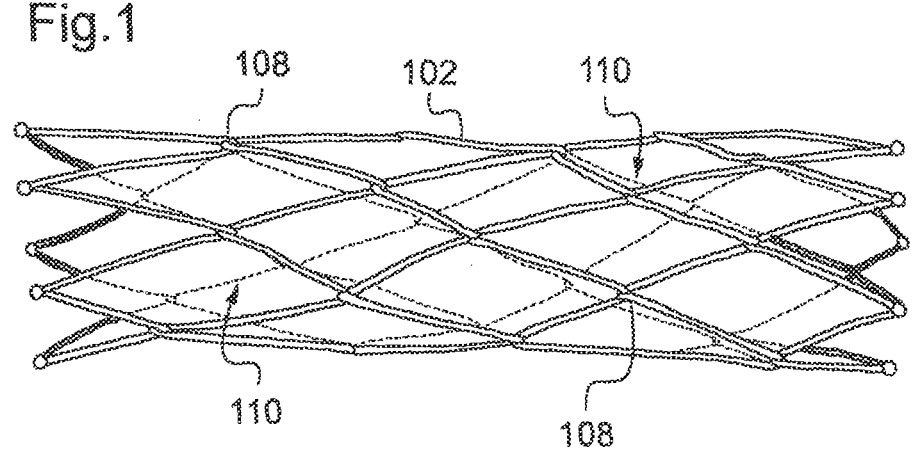

(51) Int. Cl.
 *A61F 2/90* (2013.01)
 *A61F 2/856* (2013.01)
 *A61F 2/06* (2013.01)
 *A61F 2/82* (2013.01)

(52) U.S. Cl.
 CPC ... *A61F2230/005* (2013.01); *A61F 2230/0054* (2013.01); *A61F 2250/0063* (2013.01)

(56) References Cited

U.S. PATENT DOCUMENTS

| | | | | |
|---|---|---|---|---|
| 8,721,710 B2* | 5/2014 | Waysbeyn | ......... | A61B 17/3478 606/151 |
| 8,753,386 B2* | 6/2014 | Shaw | ........ | A61F 2/07 623/1.11 |
| 8,808,358 B2* | 8/2014 | Khoury | ........ | A61F 2/07 623/1.35 |
| 8,864,819 B2* | 10/2014 | Hartley | ........ | A61F 2/07 623/1.13 |
| 8,870,946 B1* | 10/2014 | Quinn | ........ | A61F 2/07 623/1.13 |
| 8,968,389 B2* | 3/2015 | Greenberg | ........ | A61F 2/954 623/1.24 |
| 8,992,593 B2* | 3/2015 | Chuter | ........ | A61F 2/07 623/1.13 |
| 9,034,027 B2* | 5/2015 | Ivancev | ........ | A61F 2/07 623/1.13 |
| 2005/0288765 A1* | 12/2005 | Taheri | ........ | A61B 17/00234 623/1.12 |
| 2010/0241218 A1* | 9/2010 | Bruszewski | ........ | A61F 2/064 623/1.28 |
| 2014/0200651 A1* | 7/2014 | Chuter | ........ | A61F 2/07 623/1.13 |
| 2015/0073534 A1* | 3/2015 | Roeder | ........ | A61F 2/856 623/1.35 |

FOREIGN PATENT DOCUMENTS

| | | |
|---|---|---|
| WO | 2009/102441 | 8/2009 |
| WO | 2010/024867 | 3/2010 |
| WO | 2011/070576 | 6/2011 |

* cited by examiner

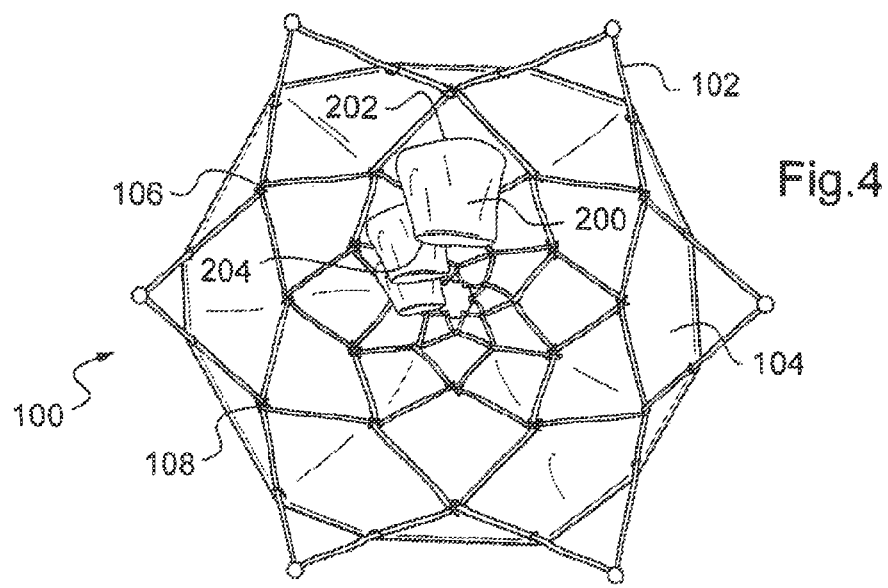
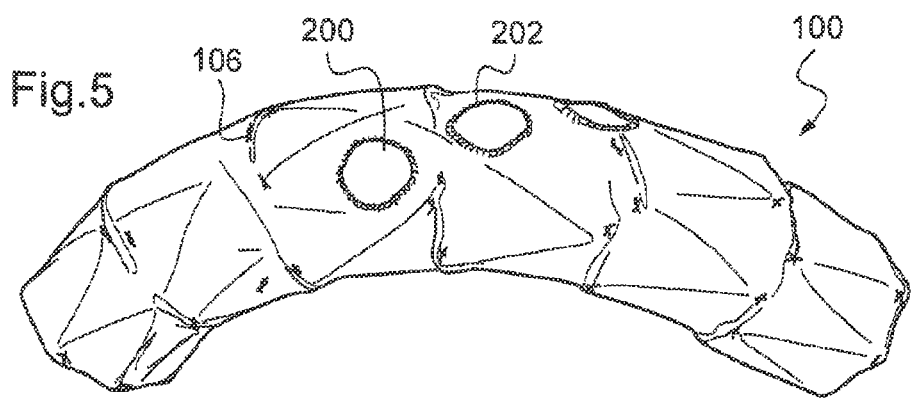
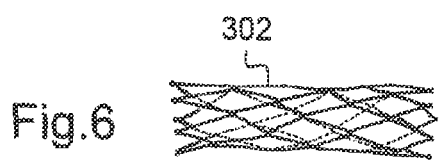
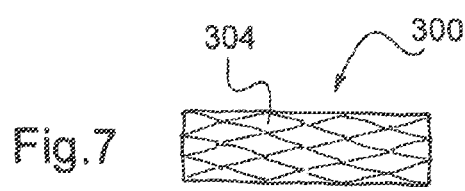
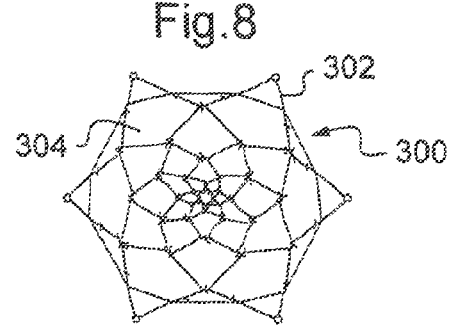

ENDOVASCULAR PROSTHESIS

BACKGROUND OF THE INVENTION

1. Field of the Invention

The present invention relates to an endovascular prosthesis.

2. Description of the Related Art

Endovascular prostheses are devices which are to be positioned inside blood vessels in order to treat aneurysmal lesions, especially in the region of the aorta.

Such prostheses are generally of tubular shape and conventionally comprise a rigid (generally metal) support structure, commonly known by the name "stent", which is covered with a synthetic fabric. Such prostheses are also known by the name vascular endoprostheses or "stent-grafts". The fabric covering the rigid support is chosen to replace the vascular wall at least partially.

It is known that, in humans, aneurysms can damage health. An aneurysm is the formation of one or more local cavities (or sacs) in the region of the wall of an artery or of a vein. These cavities fill with blood while being in communication with said artery or vein. A major risk associated with the formation of these cavities is the possibility that they may rupture. This is referred to as rupture of the aneurysm, which can lead to internal bleeding. Internal bleeding is a dangerous event which can lead to death by exsanguination.

In the art, an aneurysm can be defined as the loss of parallelism of the wall of a vessel. In other words, the walls are dilated and behave like a sac which has lower strength but is nevertheless exposed to blood pressure. As mentioned above, the main complication of aneurysms is rupture, which results in death in more than 80% of cases.

Accordingly, treatment by endovascular prosthesis aims essentially to preserve an intact blood circulation. The principle of the treatment is to exclude the aneurysmal cavity from the blood flow. This is achieved by positioning an endovascular prosthesis in the damaged artery or vein in the region of the aneurysmal cavity. More precisely, the endovascular prosthesis is arranged to fit the inside wall of the damaged artery or vein, in the region of the blood vessel-aneurysmal cavity junction. The blood vessel is thus made leak-tight with respect to the aneurysmal cavity.

The endovascular prosthesis is interposed between the healthy upstream artery and the healthy downstream artery, or the proximal neck and the distal neck, respectively. The endovascular prosthesis thus forms a leak-tight channel which acts as an artificial vessel while excluding the aneurysmal cavity.

An endovascular prosthesis is introduced by known angioplastic techniques. Among those techniques there may be mentioned especially catheterisation or arterial navigation. These techniques make it possible to avoid conventional surgery, called "open surgery", which is more invasive and which often requires the thorax or the abdomen to be opened.

Conventional endovascular prostheses thus permit the treatment of aneurysms located away from regions of origin of collaterals. However, aneurysms located close to regions of origin of collaterals (in particular close to collaterals of vital or functional importance) are more difficult to treat. Indeed, treatment by endovascular prosthesis must keep the blood supply (or perfusion) of the collaterals intact.

Aortic aneurysms are among the disorders which can be treated by means of endovascular prostheses. However, the aorta has a complex anatomy, especially at the origin of essential collaterals such as the brachiocephalic arterial trunk, the blood flow of which, which irrigates the head, must be preserved. Treatment of an aortic aneurysm by endovascular prostheses must therefore preserve an intact blood supply in the region of each bifurcation zone.

This can be achieved only with difficulty. Moreover, each patient has an anatomy which is unique to him. The endovascular prostheses known in the art are thus generally custom-made, taking account of the patient's anatomy.

The prostheses of the prior art have a steric hindrance which makes them difficult to manipulate. This gives rise to difficulties during their positioning in the body of a patient, especially in the region of considerable arterial curvature.

The scientific publication "*Fenestrated and branched devices in the pipeline*; Greenberg and Qureshi; Journal Of Vascular Surgery, Volume 52, Number 13S, 2010" discloses endovascular prostheses known in the prior art.

Document WO 2009/102441 A1 describes an endovascular prosthesis suitable for being placed in a curved region of the aorta. The prosthesis does not provide bifurcation.

Document WO 2008/107885 A2 describes an endovascular prosthesis system for generating a bifurcation in the region of the aorta.

Document WO 2011/070576 A1 describes an endovascular prosthesis system for generating a crossing in the region of the aorta.

SUMMARY OF THE INVENTION

The present invention will improve the situation.

To that end, the invention proposes an endovascular prosthesis comprising a first expandable framework and a first jacket for said first framework, said first framework and said first jacket forming a first channel when the first framework is in the expanded state. The first framework and the first jacket each have at least one opening, which openings are arranged substantially opposite one another and through which a sleeve is received, said sleeve having a first end and a second end, the perimeter of said first end being attached to the perimeter of the opening of the first jacket, while said second end extends inside said first channel.

The endovascular prosthesis of the invention has an architecture which especially allows the bifurcations encountered in the anatomy to be managed. As will be described hereinbelow, each sleeve has a dual function, which results in a freedom of manipulation both during production and during positioning of said prosthesis.

The first framework and the first jacket can each have a plurality of openings which are arranged substantially opposite one another and through which a respective sleeve is received. Each sleeve has a first end and a second end, and each perimeter of the first ends is attached to each perimeter of the openings of the first jacket, while each second end of the sleeve extends inside said first channel.

The endovascular prosthesis can further comprise a second expandable framework and a second jacket for said second framework. The second framework and the second jacket form a second channel when the second framework is in the expanded state. In this embodiment, the second channel opens into said first channel through a corresponding sleeve, while that sleeve fits at least partially the outer perimeter of said second channel to form a leak-tight bifurcation.

The endovascular prosthesis can further comprise a third expandable framework arranged inside the first channel in the region of the openings through which a sleeve is received, said third framework and the sleeve forming an operculum for said openings when the third framework is in the expanded state.

Each framework can be made of a metallic material comprising a biocompatible stainless steel, and preferably comprising a radio-opaque and/or biocompatible material.

The jacket can be made of a woven material, preferably a woven polyester material. The jacket can also be made to comprise a porous membrane, preferably a membrane of polytetrafluoroethylene (PTFE).

The jacket preferably has a thickness of less than or equal to 0.4 millimeter.

Each sleeve can be made of a material substantially identical to that of each jacket.

In one embodiment, the endovascular prosthesis has a first channel having a length of from 30 mm to 250 mm and having a diameter of from 10 mm to 50 mm. In this embodiment, each sleeve has a length of from 10 mm to 150 mm (for example from 5 mm to 30 mm) and a diameter of from 6 mm to 20 mm.

The first expandable framework can comprise an expandable metal grating. In this embodiment, the first jacket is fixed to the expandable metal grating by stitches. The jacket can be fixed on the inside or outside of the grating.

In one embodiment, the perimeter of each first end of a sleeve is attached by stitching to each perimeter of an opening of the corresponding first jacket.

The invention relates also to a kit for an endovascular prosthesis, comprising:
a) a first expandable framework and a first jacket for said first framework, said first framework and said first jacket being arranged to form a first channel when said first framework is in the expanded state,
b) a second expandable framework and a second jacket for said second framework, said second framework and said second jacket being arranged to form a second channel when the second framework is in the expanded state.

In this kit, the first framework and the first jacket each have at least one opening, which openings are arranged substantially opposite one another and through which a sleeve is received, said sleeve having a first end and a second end, the perimeter of said first end being attached to the perimeter of the opening of the first jacket, while said second end extends inside said first channel.

The kit can further comprise a third expandable framework which is to be arranged inside said first channel in the region of the openings through which a sleeve is received.

BRIEF DESCRIPTION OF THE DRAWING FIGURES

Figure 2:
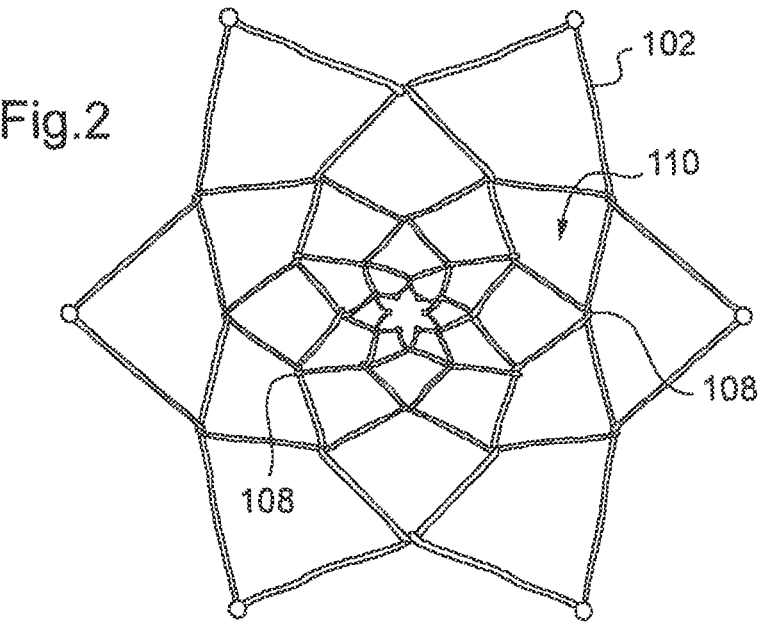
Figure 3:
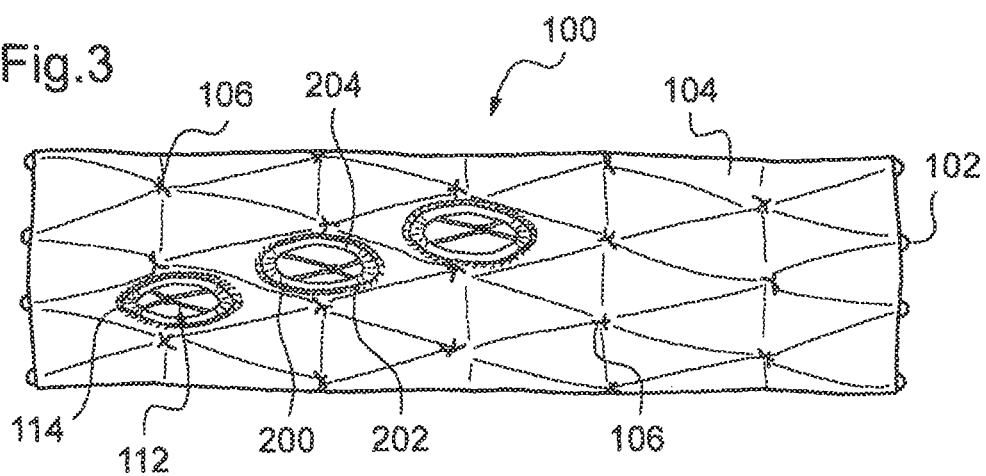
Figure 9:
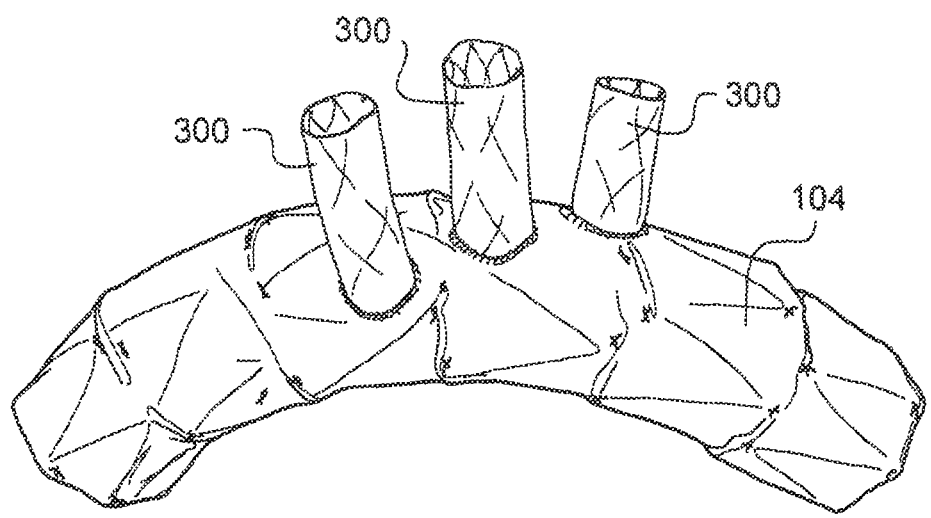
Figure 10:
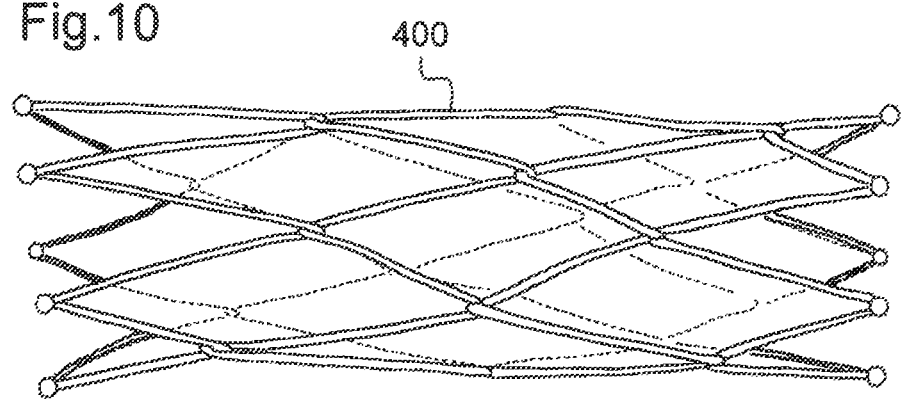
Figure 11:
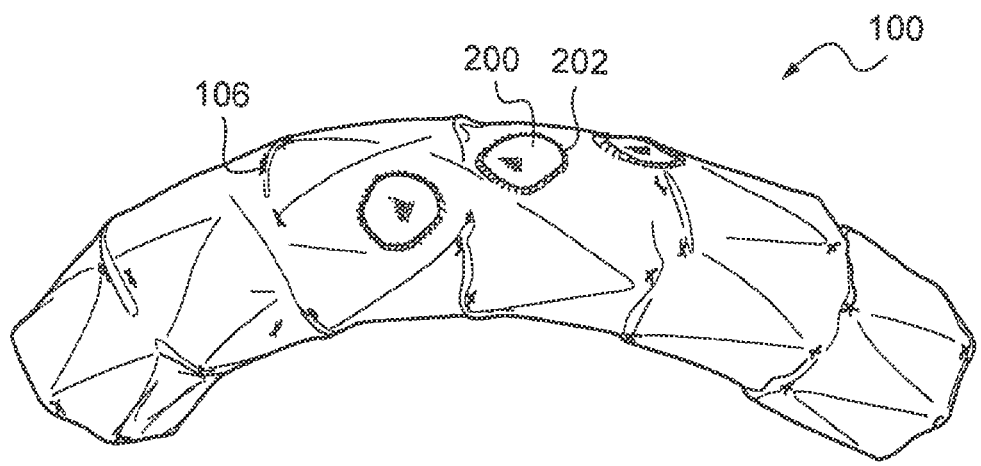
Figure 12:
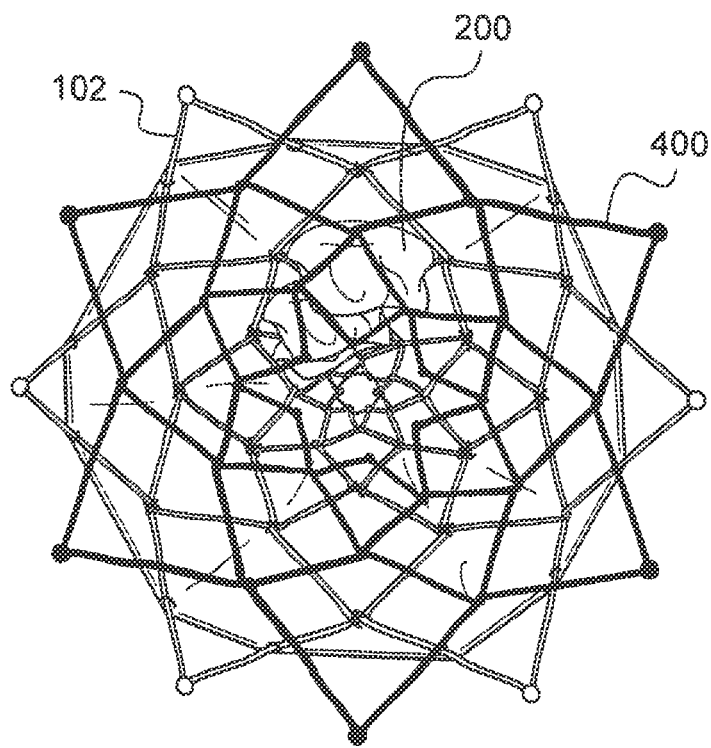

Other advantages and features of the invention will become apparent upon reading the detailed description below and from the accompanying drawings, in which:

FIG. 1 shows a front view of a first expandable framework of the endovascular prosthesis of the invention, FIG. 2 shows a side view of the first expandable framework of FIG. 1, FIG. 3 shows a front view of the first expandable framework of FIG. 1 provided with a first jacket of the endovascular prosthesis of the invention, FIG. 4 shows a side view of the first expandable framework provided with a first sleeve of the endovascular prosthesis of FIG. 3, FIG. 5 shows a perspective view of an endovascular prosthesis of the invention in the curved state, FIG. 6 shows a front view of a second expandable framework of the endovascular prosthesis according to an embodiment of the invention, FIG. 7 shows a front view of the second expandable framework of FIG. 6 provided with a second jacket of the endovascular prosthesis according to an embodiment of the invention, FIG. 8 shows a side view of the second expandable framework provided with a second jacket of the endovascular prosthesis of FIG. 7, FIG. 9 shows a perspective view of an endovascular prosthesis according to an embodiment of the invention, FIG. 10 shows a front view of a third expandable framework of the endovascular prosthesis according to an embodiment of the invention, FIG. 11 shows a perspective view of an endovascular prosthesis provided with a third expandable framework according to another embodiment of the invention, and FIG. 12 shows a side view of the endovascular prosthesis provided with a third expandable framework according to another embodiment of the invention.

The drawings and the description below mainly contain elements of a specific nature. The drawings show, at least in part, aspects which are difficult to describe other than by means of the drawing. They form an integral part of the description and may therefore not only serve for better understanding of the present invention but also contribute to the definition thereof, where appropriate.

DETAILED DESCRIPTION OF THE INVENTION

The present invention provides an assembly of a plurality of particular structural and architectural elements for avoiding the disadvantages of the prior art. Generally, the endovascular prosthesis of the invention comprises a main channel provided with bifurcation elements. According to one embodiment, each bifurcation element permits a leak-tight connection with another channel in order to manage the bifurcations encountered in the anatomy. According to another embodiment, each bifurcation element permits leak-tight closing of the main channel. In other words, each bifurcation element can, as desired, be connected to another channel or closed off in order to make the main channel leak-tight.

To that end, the endovascular prosthesis especially provides one or more sleeves which extend inside the main channel. The size of each sleeve is chosen to perform its dual bifurcation-closing function. The size is also chosen as a function of the diameter of the main channel.

As mentioned above, the structure and architecture of the endovascular prosthesis of the invention provide particular features which will now be described with reference to the drawings.

FIG. 1 shows a front view of a first expandable framework 102 of the endovascular prosthesis of the invention. The framework 102 is shown in the expanded state. It is formed by a mesh made of a metallic material. The mesh can be produced by braiding or intertwining wires. There is obtained a mesh structure having knots 108 where said wires are intertwined. The general appearance of the first expandable framework 102 is tubular, as can be seen more precisely in FIG. 2, which shows a side view of the first expandable framework 102 of FIG. 1. FIG. 2 also shows that the first expandable framework 102 defines an empty inside space.

The mesh of the embodiment of FIGS. 1 and 2 has a regular structure formed by a series of polygons, and more precisely by a series of diamonds. Because the polygons are formed by wires, they are voids. Consequently, each polygon comprises an opening 110.

The metallic material used to construct the first expandable framework 102 is at least partially flexible. The framework 102 can thus be compressed over its entire length so that it can be fed into a catheter and positioned in the body of a patient.

The material of the first expandable framework 102 can be stainless steel. The material is chosen to be biocompatible and preferably comprises a radio-opaque material to assist with manipulation during positioning of the prosthesis in a patient, as well as to permit post-operative radioanalysis. Indeed, a prosthesis comprising a radio-opaque material permits accurate identification during medical imaging by means of X-ray-type electromagnetic radiation (radiography). A material of the cobalt-chromium alloy type can especially be provided.

FIG. 3 shows a front view of the first expandable framework 102 provided with a first jacket 104. The jacket 104 is attached on the outside of the framework 102 by stitches 106 formed in the region of the knots 108. The first expandable framework 102 together with the first jacket 104 thus form a first channel 100. FIG. 4 shows a side view of the first channel 100. The jacket 104 is made of a woven material, preferably a woven polyester material.

The first jacket 104 comprises at least one opening 112. Each opening 112 of the first jacket 104 is formed by a cut in said jacket 104. Each opening 112 of the first jacket 104 is thus delimited circumferentially by a perimeter 114 of the opening 112 of the first jacket. The perimeter 114 of the opening of the first jacket can especially have a circular, elliptical or ovoid shape. A circular shape is generally preferred.

Each opening 112 of the first jacket is arranged substantially opposite an opening 110 of the first expandable framework 102. A sleeve 200 is received through each respective opening 110, 112. The sleeve 200 has a first end 202 and a second end 204. The perimeter of said first end 202 is attached to the perimeter 114 of the opening 112 of the first jacket 104. In one embodiment, the first end 202 is stitched along the perimeter 114 of the opening 112 of the first jacket 104. The second end 204 extends inside the first channel 100.

Each sleeve 200 is made of a woven material analogous to that of the first jacket 104, for example of polyester.

FIG. 5 shows a perspective view of an endovascular prosthesis of the invention and shows the channel 100 in the curved state. The first expandable framework 102 is at least partially flexible in order to allow the prosthesis to adapt according to the anatomy of the blood vessel. The channel 100 formed by the framework 102 covered by its jacket 104 is thus able to fit the inside wall of the blood vessel into which it is introduced. Each sleeve 200 may or may not be arranged opposite a blood vessel bifurcation.

FIG. 6 shows a front view of a second expandable framework 302 of the endovascular prosthesis according to an embodiment of the invention. The structure and architecture are comparable to the first expandable framework 102. It is in fact formed by braiding or intertwining wires of a material analogous to that of the first framework 102.

However, the size of the second expandable framework 302 is reduced as compared with that of the first expandable framework 102. The size of the second expandable framework 302 is thus chosen to form a second channel 300 of reduced diameter as compared with the first channel 100, as is shown in FIGS. 7 and 8. FIG. 7 shows a front view of the second expandable framework 302 provided with a second jacket 304, which together form the second channel 300 of the endovascular prosthesis according to an embodiment of the invention. FIG. 8 shows a side view of the second channel 300.

FIG. 9 shows a perspective view of an endovascular prosthesis according to an embodiment of the invention. Each second channel 300 is introduced into a corresponding sleeve 200. The outer perimeter of a second channel 300 fits the inner perimeter of the corresponding sleeve 200. This provides good leak tightness. In this manner, the endovascular prosthesis of the invention manages blood vessel bifurcations that are encountered in the anatomy of a patient. According to one embodiment, the sleeve is made of a woven polyester material, which provides a certain margin of expansion of the inside diameter of said sleeve 200. This margin of expansion permits radial dilation of the sleeve 200 when the second channel 300 is introduced into said sleeve 200. The sleeve 200 shapes itself around the second channel 300 to maximise the tightness of the bifurcation.

In practice, it must be understood that the first channel 100 must ideally fill a maximum volume inside the aneurysmal blood vessel. To that end, the invention proposes especially that each sleeve 200 extends inside said channel 100 and thus does not impede the maximum expansion thereof. Good expansion of the channel 100 allows it substantially to fit the inside wall of the blood vessel and thus isolate and exclude the aneurysmal cavity from the blood flow.

Each sleeve 200 does not have a metallic framework and hangs freely inside the channel 100. The sleeve therefore does not have a rigid structure. This offers flexibility of manipulation and especially offers the possibility of using a sleeve as a bifurcation point (see FIG. 9) or as a closing element.

FIG. 10 shows a front view of a third expandable framework 400 of the endovascular prosthesis according to an embodiment of the invention. The framework 400 is produced by braiding or intertwining a material analogous to the first expandable framework 102. The mesh can be different from the first expandable framework 102. It is provided that the diameter of the third expandable framework 400 in the expanded state is greater than the diameter of the first expandable framework 102 in the expanded state and consequently greater than the inside diameter of the first channel 100.

According to one embodiment, the third expandable framework 400 is introduced into the first channel 100 in the region of at least one sleeve 200.

FIG. 11 shows a perspective view of an endovascular prosthesis provided with a third expandable framework, and FIG. 12 shows a side view of the endovascular prosthesis provided with a third expandable framework.

During the introduction, the third expandable framework 400 is in a compressed state. When the third expandable framework 400 is positioned in the region of at least one sleeve 200, it expands and its diameter increases gradually until it fits the inside wall of the first channel 100. The sleeve 200 extending in a flexible manner inside the first channel 100 is then flattened against the inside wall of the first channel 100 by bending and thus forming a closure of the opening 112 of the first jacket. In this case, the sleeve 200 forms a leak-tight operculum for the openings 112.

According to one embodiment, the first channel 100 has a length of from 30 to 250 mm and a diameter of from 10 to 50 mm. Each sleeve 200 has a length of from 10 to 150 mm and a diameter of from 6 to 30 mm. Each second channel 300 has a length of from 10 to 150 mm and a diameter of from 6 to 30 mm. Each third expandable framework 400 has a length of from 30 to 250 mm and a diameter of from 10 to 50 mm.

The endovascular prosthesis according to the invention offers a freedom of manipulation to the hospital practitioner especially by virtue of its dual bifurcation/closing function. Techniques of positioning endovascular prostheses by means of a catheter are sometimes difficult to carry out for anatomical reasons. When the positioning of a bifurcation between a first channel 100 and a second channel 300 presents complications, the invention allows the first channel 100 to be made leak-tight by the introduction of a third expandable framework 400. The bifurcation and its blood supply (or perfusion) can then be treated separately, for example by means of a bypass.

The invention relates also to a process for fitting an endovascular prosthesis in a patient.

The process of the invention comprises the following steps:
a) providing an endovascular prosthesis comprising a first expandable framework and a first jacket for said first framework, said first framework and said first jacket forming a first channel when the first framework is in the expanded state, the first framework and the first jacket each having at least one opening, which openings are arranged substantially opposite one another and through which a sleeve is received, said sleeve having a first end and a second end, the perimeter of said first end being attached to the perimeter of the opening of the first jacket, while said second end extends inside said first channel, and
b) positioning the endovascular prosthesis provided in step a) in an individual.

According to one embodiment, the process of the invention can further comprise the following steps:
c) providing a second expandable framework and a second jacket for said second framework, said second framework and said second jacket forming a second channel when the second framework is in the expanded state, and
d) positioning said second channel in the individual of step b), said second channel being positioned to open into said first channel through a corresponding sleeve, while the sleeve fits at least partially the outer perimeter of said second channel to form a leak-tight bifurcation.

According to another embodiment, the process of the invention can further comprise the following steps:
e) providing a third expandable framework, and
f) positioning the third expandable framework in the individual of step b), said third expandable framework being positioned inside the first channel in the region of the openings through which a sleeve is received, said third framework and said sleeve forming an operculum for said openings when the third framework is in the expanded state in the first channel.

The positioning operations referred to above are generally carried out by angioplastic methods. Among those methods there may be mentioned especially surgical interventions by catheterisation.

The present invention has been described substantially with reference to the human anatomy and specifically with reference to the anatomy encountered in the region of the aortic arch. However, the invention can be used in other parts of the human body and can also be used in any other mammal The invention accordingly proposes an endovascular prosthesis or vascular endoprosthesis comprising a first expandable element made of a rigid framework covered with a membrane formed by a synthetic fabric. In the expanded state, this element forms the main channel of the vascular endoprosthesis. In addition to its two ends, the first channel or "main channel" comprises at least one lateral opening in the membrane. This opening comprises a membrane sleeve (formed by the synthetic fabric) directed towards the inside of the lumen of the main channel. This sleeve can be called an "invaginated sleeve". At the lateral opening, the membrane of the main channel and that of the invaginated sleeve are in absolute continuity. Unlike the main channel, the invaginated sleeve does not have a rigid framework. The lateral opening and the invaginated sleeve of the main channel are to be positioned opposite a vital or functional collateral in order to receive a second vascular endoprosthesis. The second vascular endoprosthesis is formed by an expandable rigid framework lined with a membrane and is to extend from the lumen of the main channel to the first few centimeters of the vital or functional collateral or "secondary channel".

The invaginated sleeve not only provides the connection and leak tightness between the main channel and the secondary channel but also, as will be described hereinbelow, the freedom of manipulation during fitting.

According to the anatomy to be treated, the main channel can comprise one or more invaginated sleeves for receiving one or more secondary channels. The main channel and the secondary channel comprise a rigid, for example metallic, framework lined with a fine blood-tight membrane which has demonstrated its suitability for replacing the arterial wall in humans. The membranes that are most often used within this context are made of woven or knitted textile of polyester fibres or equivalent nonwovens of polytetrafluoroethylene or PTFE. The change from the compressed form to the expanded form is based on the ability of the rigid framework to deform in the elastic, supra-elastic or plastic domain. The thickness of the membrane is advantageously less than 0.4 mm for use in humans.

The invaginated sleeve can be produced using the same membrane as that of the main channel or a membrane that is finer or whose elasticity allows the whole to be given better leak tightness. The membrane used for the invaginated sleeve is also suitable for replacing the arterial wall in humans. A notable element of the invention is that the invaginated sleeve is not provided with a rigid framework. At the orifice of the membrane of the main channel, the outer end of the invaginated sleeve is substantially in continuity with that of the membrane of the main channel. This continuity provides not only the mechanical connection but also the leak tightness. It can be obtained by stitching, adhesive bonding, welding or other methods or alternatively by a combination of methods. The inner end of the invaginated sleeve is "free" inside the lumen of the main channel or at most is fixed to the membrane of the main channel at one point in order to give it direction.

The technique of fitting the system for treating a single collateral comprises especially the following steps:
1) The main channel is deployed so that its proximal end is located substantially in the proximal neck of the aneurysm and its distal end is located substantially in the distal neck of the aneurysm. The outer orifice of the invaginated sleeve is positioned substantially opposite the ostium of the treated collateral in the aneurysm.
2) The invaginated sleeve is catheterised either starting from the treated collateral or starting from the lumen of the main channel with the aid of a flexible metal guide.
3) The secondary channel is deployed, after being slipped coaxially onto the guide, so that its proximal end is located in the lumen of the main channel and its distal end is located in the lumen of the treated collateral, in a healthy region. Contact between the membrane of the invaginated sleeve and the membrane of the secondary channel must be sufficiently lengthy and intimate to ensure perfect leak tightness between the two channels. By contrast, the final positioning and the angle of connection between the two channels depend on the anatomy being treated.
4) In the case of failure of the catheterisation of the invaginated sleeve, a certain degree of leak-tightness thereof is provided by its collapse (or folding) owing to the pressure which then prevails in the main channel. The main channel then behaves like a conventional vascular endoprosthesis. The continued existence of this situation can be ensured by the fitting of a second conventional vascular endoprosthesis which has dimensions which correspond substantially to those of the main channel and which is deployed inside the latter, flattening the invaginated sleeve against its inner face and thus closing its lateral orifice. In this case, the perfusion (or irrigation) of the vital or functional collateral is ensured by other means, for example by means of a bypass. The aim of this "rescue" step is especially to avoid re-perfusion (re-irrigation) of the aneurysmal sac by the collateral.

The dimensions of the prosthesis of the invention depend substantially on the treated anatomy. Generally, the main channel has a diameter, which may or may not be constant, of from 10 to 50 mm and a length of from 30 to 250 mm. Generally, the secondary channel has a diameter, which may or may not be constant, of from 6 to 30 mm and a length of from 10 to 150 mm. Generally, the invaginated sleeve has a diameter, which may or may not be constant, of from 6 to 30 mm and a length of from 10 to 150 mm.

The rigid framework is generally metallic with elastic deformation. The different metallic structures and the membranes (synthetic fabrics) are assembled by stitching by means of braided synthetic threads, while the membrane of all the elements and of the sleeve is produced by weaving polyester. However, the construction of the elements can employ other rigid and membranous materials and other methods of assembly.

In a particular embodiment, the invention can also be defined as follows:

Vascular endoprosthesis comprising a first expandable framework and a first jacket for said first framework, said first framework and said first jacket forming a first channel when the first framework is in the expanded state, characterised in that the first framework and the first jacket each have at least one opening, which openings are arranged substantially opposite one another and through which a flexible sleeve is received, said flexible sleeve being without a framework and having a first end and a second end, the perimeter of said first end being attached to the perimeter of the opening of the first jacket, while said second end extends inside said first channel.

According to this embodiment, the kit of the invention can be defined as follows:

Kit for an endovascular prosthesis, comprising:
a) a first expandable framework and a first jacket for said first framework, said first framework and said first jacket being arranged to form a first channel when the first framework is in the expanded state,
b) a second expandable framework and a second jacket for said second framework, said second framework and said second jacket being arranged to form a second channel when the second framework is in the expanded state,
characterised in that the first expandable framework and the first jacket each have at least one opening, which openings are arranged substantially opposite one another and through which a flexible sleeve is received, said flexible sleeve being without a framework and having a first end and a second end, the perimeter of said first end being attached to the perimeter of the opening of the first jacket, while said second end extends inside said first channel.

The flexible characteristic of the sleeve confers thereon especially a dual function. Accordingly, in a first position the sleeve performs the function of a bifurcation point, while in a second position the sleeve performs the function of a closing element.

The vascular endoprosthesis and/or the kit as defined above therefore comprise(s) a sleeve that forms a bifurcation point in a first position and that forms a closing element in a second position.

The invention claimed is:

1. An endovascular prosthesis comprising:
a first expandable framework; and
a first jacket for said first framework, said first framework and said first jacket forming a first channel when the first framework is in an expanded state, wherein
the first framework and the first jacket each have at least one opening, which openings are arranged substantially opposite one another and through which a sleeve is received, said sleeve having a first end and a second end, the perimeter of said first end being attached to the perimeter of the opening of the first jacket, while said second end extends inside said first channel, and wherein
the sleeve does not have a framework.

2. The endovascular prosthesis according to claim 1, wherein the first expandable framework and the first jacket each have a plurality of openings which are arranged substantially opposite one another and through which a sleeve is received, each sleeve having a first end and a second end, each perimeter of the first ends being attached to each perimeter of the openings of the first jacket, while each second end extends inside said first channel.

3. The endovascular prosthesis according to claim 1, wherein the prosthesis further comprises a second expandable framework and a second jacket for said second framework, said second framework and said second jacket forming a second channel when the second framework is in the expanded state, and in that said second channel opens into said first channel through a corresponding sleeve, while the sleeve fits at least partially the outer perimeter of said second channel to form a leak-tight bifurcation.

4. The endovascular prosthesis according to claim 1, wherein the prosthesis further comprises a third expandable framework arranged inside the first channel in the region of the openings through which a sleeve is received, said third expandable framework and said sleeve forming an operculum for said openings when the third expandable framework is in the expanded state inside said first channel.

5. The endovascular prosthesis according to claim 1, wherein each framework is made of a metallic material comprising a biocompatible stainless steel, and preferably comprising a radio-opaque material.

6. The endovascular prosthesis according to claim 1, wherein each jacket is made of a woven material, preferably of a woven polyester material.

7. The endovascular prosthesis according to claim 1, wherein each jacket comprises a porous membrane, preferably a membrane of polytetrafluoroethylene.

8. The endovascular prosthesis according to claim 1, wherein each sleeve is made of a material which is substantially identical to that of each jacket.

9. The endovascular prosthesis according to claim 1, wherein said first channel has a length of from 30 mm to 250 mm and a diameter of from 10 mm to 50 mm, and wherein each sleeve has a length of from 10 mm to 150 mm and a diameter of from 6 mm to 20 mm.

10. The endovascular prosthesis according to claim 1, wherein each jacket has a thickness of less than or equal to 0.4 millimeter.

11. The endovascular prosthesis according to claim 1, wherein the first expandable framework comprises an expandable metal grating, and wherein the first jacket is fixed to the expandable metal grating by stitches.

12. The endovascular prosthesis according to claim 1, wherein each perimeter of each first end of a sleeve is attached by stitching to each perimeter of an opening of the corresponding first jacket.

13. A kit for an endovascular prosthesis, comprising:
  a) a first expandable framework and a first jacket for said first framework, said first framework and said first jacket being arranged to form a first channel when the first framework is in the expanded state; and
  b) a second expandable framework and a second jacket for said second framework, said second framework and said second jacket being arranged to form a second channel when the second framework is in the expanded state,
  wherein the first expandable framework and the first jacket each have at least one opening, which openings are arranged substantially opposite one another and through which a sleeve is received, said sleeve having a first end and a second end, the perimeter of said first end being attached to the perimeter of the opening of the first jacket, while said second end extends inside said first channel, and wherein
  the sleeve does not have a framework.

14. The kit according to claim 13, further comprising a third expandable framework which is to be arranged inside said first channel in the region of the openings through which a sleeve is received.

15. The endovascular prosthesis according to claim 1, wherein the sleeve is formed from woven polyester having a margin of expansion that permits radial expansion of the sleeve.

16. The endovascular prosthesis according to claim 1, wherein the sleeve is a bifurcation point or a closing element.

17. The kit according to claim 13, wherein the sleeve is formed from woven polyester having a margin of expansion that permits radial expansion of the sleeve.

18. The kit according to claim 13, wherein the sleeve is a bifurcation point or a closing element.

* * * * *